US006561993B2

(12) United States Patent
Adapathya et al.

(10) Patent No.: US 6,561,993 B2
(45) Date of Patent: May 13, 2003

(54) DEVICE DRIVER SYSTEM FOR MINIMIZING ADVERSE TREMOR EFFECTS DURING USE OF POINTING DEVICES

(75) Inventors: Ravi Shankarnarayan Adapathya, Durham, NC (US); David Frederick Champion, Durham, NC (US); Alan Joseph Happ, Raleigh, NC (US); Brad Michael Lawrence, Durham, NC (US); Kevin Laverne Schultz, Raleigh, NC (US)

(73) Assignee: International Business Machines Corporation, Armonk, NY (US)

( * ) Notice: Subject to any disclaimer, the term of this patent is extended or adjusted under 35 U.S.C. 154(b) by 144 days.

(21) Appl. No.: 09/793,184

(22) Filed: Feb. 26, 2001

(65) Prior Publication Data

US 2002/0120217 A1 Aug. 29, 2002

(51) Int. Cl.[7] .............................. A61B 5/103; G06F 3/00
(52) U.S. Cl. ...................................... 600/595; 345/163
(58) Field of Search ................................. 600/531, 595; 345/856–858, 157–158, 163–167, 161

(56) References Cited

U.S. PATENT DOCUMENTS

| 4,306,291 A | 12/1981 | Zilm et al. |
| 5,265,619 A | 11/1993 | Comby et al. |
| 5,293,879 A | 3/1994 | Vonk et al. |
| 5,573,011 A | 11/1996 | Felsing |
| 5,783,997 A | 7/1998 | Saitoh et al. |
| 5,964,720 A | 10/1999 | Pelz |

FOREIGN PATENT DOCUMENTS

| JP | 3-116219 | * | 5/1991 |
| JP | 8-137608 | * | 5/1993 |
| JP | 6-166901 | * | 9/1994 |
| JP | 7-64694 | * | 3/1995 |
| JP | 7-64713 | * | 3/1995 |
| JP | 10-301702 | * | 11/1998 |
| JP | 2000-200151 | * | 7/2000 |

OTHER PUBLICATIONS

C. N. Riviere & N. Thakor, "Modeling & Canceling Tremor in Human–Machine Interfaces," IEEE Engr. in Med. & Biol., May/Jun. 1996, pp. 29–36.*
S. Pledgie et al., "Tremor Suppression Through Impedance Control," IEEE Trans. on Rehab. Engr., vol. 8, No. 1, Mar. 2000, pp. 53–59.*
J. Gonzalez, "A New Approach to Suppressing Abnormal Tremor Through Signal Equalization," Masters' Thesis for Univ. of Del., Fall 1995.*

(List continued on next page.)

Primary Examiner—John A. Jeffery
(74) Attorney, Agent, or Firm—Sawyer Law Group LLP

(57) ABSTRACT

A system and method for minimizing essential tremor effects while utilizing a pointing device on a computer system is disclosed. The system and method comprises obtaining an individual's tremor characteristics and calculating the frequency components of the tremor to obtain digital filter coefficients. The method and system further includes creating a calibration profile comprised of digital filter coefficient that plugs into a pointing device driver; and utilizing the modified device driver to eliminate the effects of the essential tremors. The system and method includes a software tuning algorithm used to obtain an individual's tremor characteristics. A spectral analysis system will calculate the frequency components of the tremor and digital filter coefficients will be saved as a profile. The appropriate filter coefficients will be passed to a device driver via the profile. The modified device driver will filter the pointing device input data based on the filter coefficients and eliminate tremor effects from the on-screen pointer. Because the profile is transferable, if a device driver capable of accepting the profile plug-in were already installed on a computer, the profile could be loaded and used immediately on the computer without the need for re-calibration.

22 Claims, 3 Drawing Sheets

OTHER PUBLICATIONS

J. Gonzalez et al, "A Customized Optimal Filter for Eliminating Operator's Tremor," Proc. SPIE Intl. Symp. on Intell. Sys. & Adv. Mfr., Oct. 1995.*

C. Riviere & N. Thakor, "Adaptive Human–Machine Interface for Persons With Tremor," IEEE–EMBC & CMBEC, 1995, pp. 1193–1194.*

C. Riviere et al, "Adaptive Canceling of Physiological Tremor for Improved Precision in Micrsurgery," IEEE Trans. Biomed. Engr., vol. 45, No. 7, Jul. 1998, pp. 839–846.*

J. Gonzalez et al, "Filtering Involuntary Motion of People with Tremor Disability Using Optimal Equalization," Proc. IEEE Intl. Conf. Sys, Man, and Cybernetics, 1995.*

C. Riviere & N. Thakor, "Suppressing Pathological Tremor During Dextrous Teleoperation," IEEE–EMBC & CMBEC, 1995, pp. 1195–1196.*

Univ. of Del., "Rehabilitation Robotics: Pathological Tremor Suppression," http://mechsys4.me.udel.edu/students/pledgie/Rehab_tremor.html.*

J. Phillips et al, "Cursor Control Device Characteristics" date unknown.*

J. Phillips et al, "A Kinematic Analysis of Computer Mouse Movements," date unknown.*

P. Feys et al, "Assistive Technology to Improve PC Interaction for People with Intention Tremor," J. Rehab. Res. & Dev., vol. 38, No. 2, Mar./Apr. 2001.*

* cited by examiner

DEVICE DRIVER SYSTEM FOR MINIMIZING ADVERSE TREMOR EFFECTS DURING USE OF POINTING DEVICES

FIELD OF THE INVENTION

The present invention relates generally to computer systems and more particularly to the use of pointing devices in such computer systems.

BACKGROUND OF THE INVENTION

FIG. 1 is a pictorial view of a computer system. The computer system includes a monitor 12 with a keyboard 16 and a computing unit coupled to the monitor 14. Typically, connected to the computing unit is a pointing device such as a mouse 18 which is controlled by a user's hand 20. In such a system, if a person has some type of tremor disorder it could affect the use of the pointing device 18 by the user 20.

Essential tremor (ET), characterized by rhythmic "back and forth" movement from involuntary musculature contraction, affects as many as 1 in 20 people over 40 and 1 in 5 people over 65. With the exception of stroke, essential tremor is more common than any other neurological disease, affecting over 5 million Americans. It is very difficult for people with ET to effectively use a handheld computer pointing device, such as a mouse, due to continuous hand displacement caused by tremor. Tracking tasks and tasks where the individual must click on a small target (e.g., the "close window" button in a graphical user interface) are especially difficult.

Accordingly, what is needed is a system and method for responding to essential tremors when using a pointing device that is simple, easy to implement and is acceptable to many different individuals. The present invention addresses such a need.

SUMMARY OF THE INVENTION

A system and method for minimizing essential tremor effects while utilizing a pointing device on a computer system is disclosed. The system and method comprises obtaining an individual's tremor characteristics and calculating the frequency components of the tremor to obtain digital filter coefficients. The method and system further includes creating a calibration profile comprised of the digital coefficient that plugs into a pointing device driver; and utilizing the modified device driver to eliminate the effects of the essential tremors.

The system and method includes a software tuning algorithm used to obtain an individual's tremor characteristics. A spectral analysis system will calculate the frequency components of the tremor and digital filter coefficients will be saved as a calibration profile. The system and method further includes a device driver modified by calibration profile created from the tuning algorithm. The modified device driver will filter the pointing device input data based on the filter coefficients saved in the calibration profile and eliminate tremor effects from the on-screen pointer.

Because the calibration profile is transferable, if a device driver capable of accepting the calibration profile plug-in were already installed on a computer, the profile could be loaded and used immediately on the computer without the need for re-calibration.

DETAILED DESCRIPTION

The present invention relates generally to computer systems and more particularly to the use of pointing devices in such computer systems. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

A system and method in accordance with the present invention provides for tremor elimination when utilizing computer input devices. The system utilizes a tuning algorithm and spectral analysis algorithm to capture the spectral (frequency domain) properties of an individual's tremor characteristics and save them as an individualistic calibration profile. The profile is then plugged into a device driver, and the modified device driver eliminates the effects of tremor from the on-screen pointer.

Figure 1:
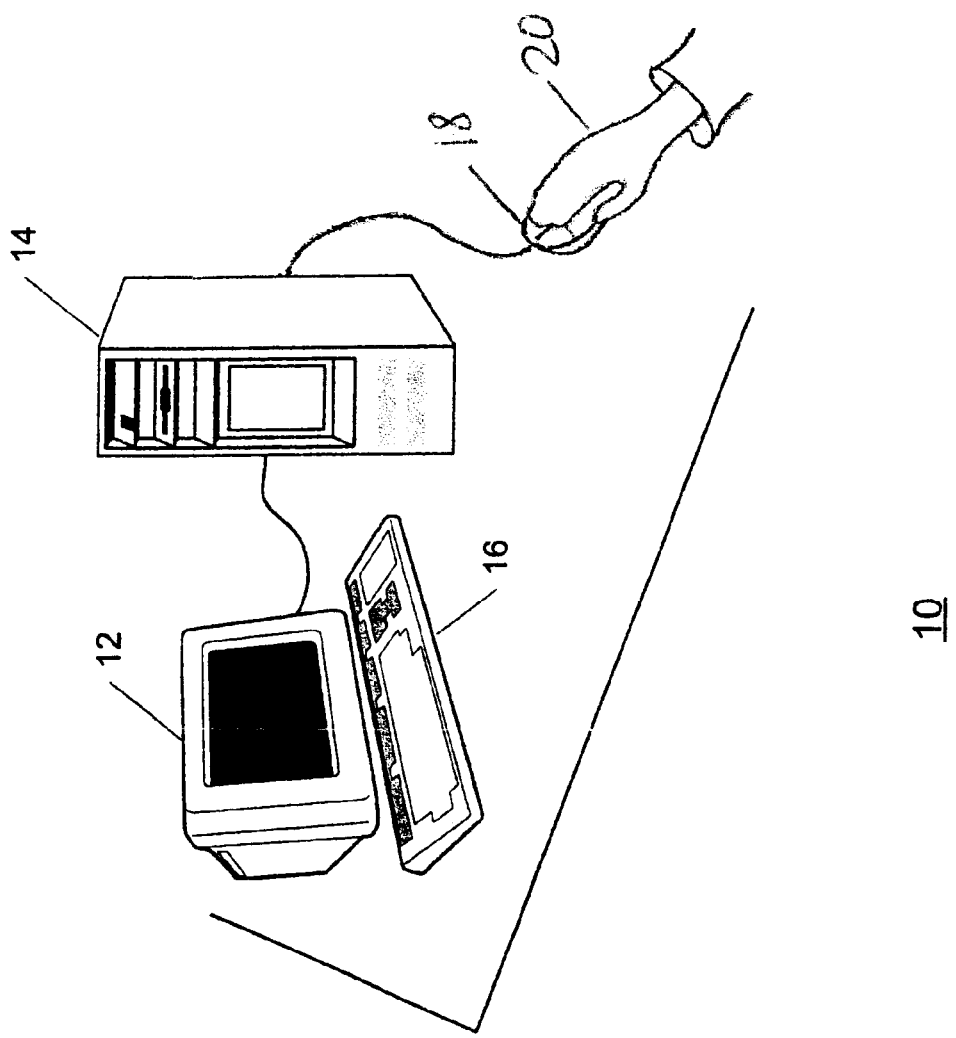
FIG. 1 is a block diagram of the typical computer system.
Figure 2:
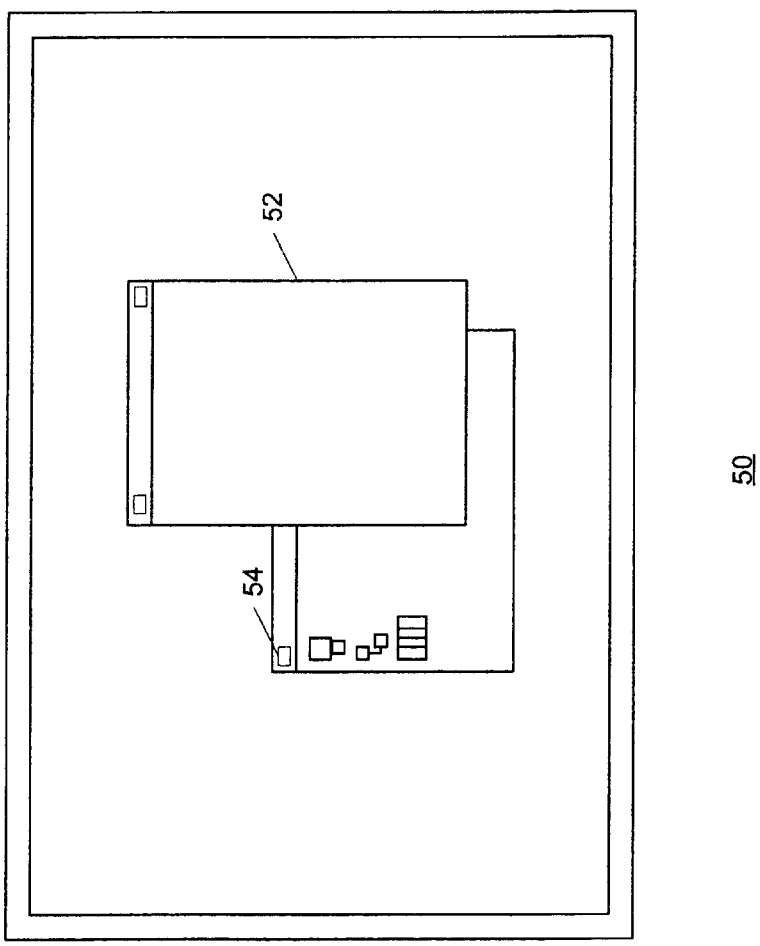
FIG. 2 is a diagram illustrating a graphical user interface in a windows environment.
Figure 3:
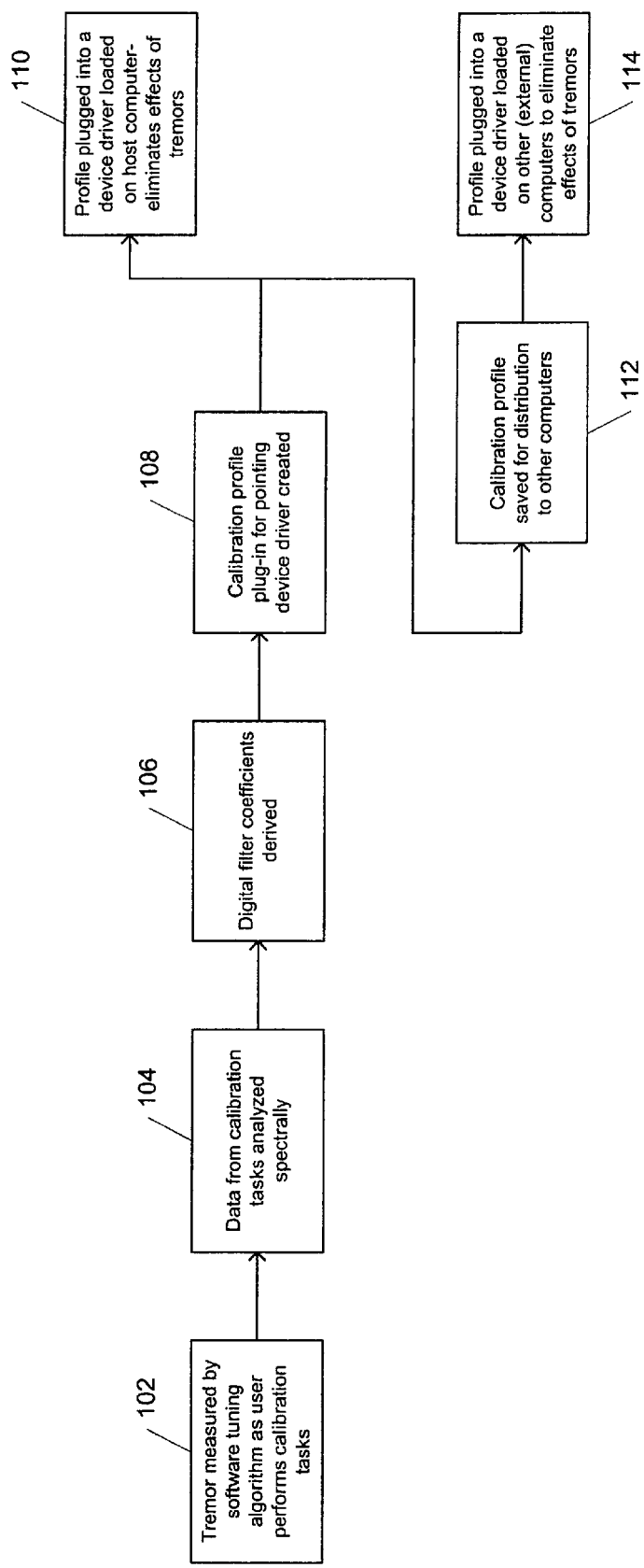
FIG. 3 is a flow chart which illustrates the process for minimizing essential tremors in accordance with the present invention.

The present invention would be utilized to allow for the optimization of the pointing device within a graphical user interface in a windows environment. To more particularly describe the features of the present invention, refer now to the following discussion in conjunction with the accompanying figures. FIG. 2 is a diagram illustrating a graphical user interface. In a such a system, the icons and buttons on the windows 52 and 54 would be manipulated by a user during common pointing device tasks. FIG. 3 is a flow chart which illustrates the process for eliminating essential tremors in accordance with the present invention.

First the tremors are measured by a software tuning algorithm as the user performs calibration tasks, via step 102. Next the data measured from those calibration tasks is analyzed spectrally from step 104. Thereafter, the digital filter coefficients are derived, via step 106. Finally, a calibration profile plug-in for a pointing device driver is built based upon those derived digital filter coefficients, via step 108. Thereafter, one of two things can be done. One is the profile can be plugged into a device driver on the host computer and the effect of tremors can then be eliminated, via step 110. In the alternative, the profile can be saved for distribution, via step 112, and then can be plugged into a device driver loaded on another computer, via step 114, and the effect of the tremors can then be eliminated.

In the present invention, a device driver utilizes a customized calibration profile that maps physical pointing device motion to on-screen pointer movement. The calibration profile is customized through a software "tuning" algorithm, which collects data as an individual performs on-screen pointing device tasks, such as tracking a linear target (simulating choosing a file or file folder from a list) and attempting to remain stationary over a specified target similar in size to a typical graphical user interface operating system control box (e.g., close, minimize, and maximize buttons: scroll boxes on scroll bars) and icons. A spectral analysis algorithm will analyze the pointing device displacement data using a spectral power density function that determines the frequency components of the signal associated with tremor. A calibration profile is then developed that contains digital filter coefficients that plug into a device driver to eliminates on-screen displacements associated with tremor by digitally filtering the frequencies associated with an individual's tremor. The data analysis and digital filtering methods used in the spectral analysis algorithm are common signal processing techniques and are used extensively.

EXAMPLE

Consider a person with ET that exhibits side to side motion of the hand that causes a pointing device to move back and forth 5 times per second. It is very difficult for this individual to follow a straight line or click on a small button, because the on-screen pointer will also move back and forth over and off of the intended target at a rate of 5 times per second. By performing the calibration tracking and targeting tasks in the tuning algorithm, the individual's tremor characteristics can be calculated. A spectral power density function described previously transforms the pointing device output data from the time domain to the frequency domain and indicates at what frequencies pointing device movement is occurring. In the data, there will be low frequencies (less than 2 Hertz) that correspond with intended movement and higher frequencies (higher than 4 Hertz) that correspond to unintended tremor-induced movements. In this case the tremor-induced movements (occurring at 5 times per second) equate to a frequency of 5 Hertz. In this example, a digital filter would be employed that removes all movement data associated with a frequency of 5 Hertz, leaving the rest of the movement data intact. The digital filter characteristics for this individual would be saved and built into a calibration profile. Implementation of this calibration profile with the accompanying device driver would cause the pointing device to respond to only intended, voluntary movements, resulting in smooth pointer icon trajectories and accurate target selection. The computer would be effectively "blind" to the tremor frequency and although the pointing device would still be moving back and forth at 5 Hertz, the on-screen pointer would not respond to these tremor-induced movements.

Accordingly, a system and method in accordance with the present invention solves the problem by filtering out repetitive tremor movements from the input stream of the pointing device, and thereby allows smoother control of the pointing cursor allowing for efficient use of the device despite the tremors. An additional potential advantage is that the customized calibration profile could be made transferable to other computers allowing someone with ET to carry their profile with them. If a device driver capable of accepting the calibration profile plug-in were already installed on a computer, the profile could be loaded and used immediately without the need for re-calibration.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for minimizing essential tremor effects while utilizing a pointing device on a computer system; the method comprising the steps of:

(a) obtaining an individual's tremor characteristics;
(b) calculating the frequency components of the tremor to obtain digital filter coefficients; and
(c) creating a calibration profile plug-in based upon the digital coefficients; and
(d) utilizing the calibration profile plug-in to recalibrate the pointing device by loading it into a pointing device driver to eliminate the effects of the essential tremors.

2. The method of claim 1 in which a software tuning algorithm performs the obtaining step (a).

3. The method of claim 1 in which a spectral analysis system performs the calculating step (b).

4. The method of claim 1 in which the digital coefficients are saved as a calibration profile plug-in.

5. The method of claim 4 in which the profile plug-in is utilized to plug into the device driver.

6. The method of claim 1 in which the utilizing step (d) comprises the step of (d1) loading the profile plug-in into a pointing device driver on a host computer.

7. The method of claim 1 in which the utilizing step comprises the step of (d1) saving the profile plug-in to distribute to other computers; and (d2) loading the profile plug-in into a pointing device driver.

8. The method of claim 4 wherein the profile maps physical pointing device motion to on-screen pointer movement.

9. The method of claim 1 wherein the obtaining step (a) comprises the step of (a1) collecting data as an individual performs on-screen calibrating tasks.

10. The method of claim 9 wherein the on-screen pointing tasks comprise calibrating a linear target and attempting to remain stationary over a specified target.

11. A computer readable medium containing program instructions for minimizing essential tremor effects while utilizing a pointing device on a computer system; the program instructions for:

(a) obtaining an individual's tremor characteristics;
(b) calculating the frequency components of the tremor to obtain digital filter coefficients;
(c) creating a calibration profile plug-in based upon the digital coefficients; and
(d) utilizing the calibration profile plug-in to recalibrate the pointing device by loading it into a pointing device driver to eliminate the effects of the essential tremors.

12. The computer readable medium of claim 11 in which a software tuning algorithm performs the obtaining step (a).

13. The computer readable medium of claim 11 in which a spectral analysis system performs the calculating step (b).

14. The computer readable medium of claim 11 in which the digital coefficients are saved as a calibration profile plug-in.

15. The computer readable medium of claim 14 in which the profile plug-in is utilized to plug into a device driver.

16. The computer readable medium of claim 11 in which the utilizing step (d) comprises the step of (d1) loading the profile plug-in into a pointing device driver on a host computer.

17. The computer readable medium of claim 11 in which the utilizing step comprises the step of (d1) saving the profile plug-in to distribute to other computers; and (d2) loading the profile plug-in into a pointing device driver on a remote computer.

18. The computer readable medium of claim 14 wherein the profile maps physical pointing device motion to on-screen pointer movement.

19. The computer readable medium of claim 11 wherein the obtaining step (a) comprises the step of (a1) collecting data as an individual performs on-screen calibrating tasks.

20. The computer readable medium of claim 19 wherein the on-screen calibrating tasks comprise tracking a linear target and attempting to remain stationary over a specified target.

21. A method for minimizing essential tremor effects while utilizing a pointing device on a computer system; the method comprising the steps of:

(a) obtaining an individual's tremor characteristics;

(b) calculating the frequency components of the tremor to obtain digital filter coefficients;

(c) creating a calibration profile plug-in based upon the digital coefficients;

(d) saving the calibration profile plug-in to distribute to other computers; and (e) loading the calibration profile plug-in into a pointing device driver.

22. A computer readable medium containing program instructions for minimizing essential tremor effects while utilizing a pointing device on a computer system; the programming instructions for:

(a) obtaining an individual's tremor characteristics;

(b) calculating the frequency components of the tremor to obtain digital filter coefficients;

(c) creating a calibration profile plug-in based upon the digital coefficients;

(d) saving the calibration profile plug-in to distribute to other computers; and (e) loading the calibration profile plug-in into a pointing device driver.

* * * * *